United States Patent [19]
Kleiner

[11] Patent Number: 5,990,337
[45] Date of Patent: Nov. 23, 1999

[54] PROCESS FOR THE PREPARATION OF 2-CYANOETHYLPHOSPHINIC ESTERS

[75] Inventor: Hanss-Jerg Kleiner, Kronberg, Germany

[73] Assignee: Ticona GmbH, Germany

[21] Appl. No.: 08/921,654

[22] Filed: Aug. 26, 1997

[30] Foreign Application Priority Data

Aug. 28, 1996 [DE] Germany .................. 196 34 706

[51] Int. Cl.$^6$ ................................. C07F 9/32
[52] U.S. Cl. ................ 558/73; 558/134; 558/145; 558/167
[58] Field of Search ................ 558/73, 134, 145, 558/167

[56] References Cited

U.S. PATENT DOCUMENTS

| | | |
|---|---|---|
| 4,594,199 | 6/1986 | Thottathil . |
| 5,051,524 | 9/1991 | Baylis . |
| 5,407,922 | 4/1995 | Marescaux et al. . |

FOREIGN PATENT DOCUMENTS

| | | |
|---|---|---|
| 0 319 479 | 6/1987 | European Pat. Off. . |
| 0 463 560 | 1/1992 | European Pat. Off. . |

OTHER PUBLICATIONS

CA:117:17188, abs of JP04029237, Jan. 1992.
CA:122:160936 abs of EP632050, Jan. 1995.
Wolfgang Froestl: "Phosphinic acid analogues of GABA" Journal of Medicinal Chemistry, Bd. 38, Nr. 17, 1995, Washington D.C., pp. 3297–3312, XP002043375.

*Primary Examiner*—Gary Geist
*Assistant Examiner*—Jean F Vollano
*Attorney, Agent, or Firm*—Connolly & Hutz

[57] ABSTRACT

The invention relates to a process for the preparation of phosphorus-containing compounds of the formula (I)

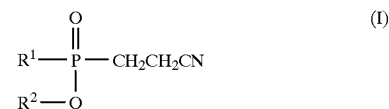

where $R^1$ and $R^2$ are identical or different and are a straight-chain or branched alkyl radical having 1 to 8 carbon atoms, a cyclohexyl-, cyclopentyl-, aryl-, halogen-, $(C_1\text{–}C_6)$-alkyl- or $(C_1\text{–}C_6)$-alkoxy-substituted aryl radical, where $R^1$ and $R^2$, together with the phosphorus atom and the oxygen atom, can also form a ring, in particular an oxaphosphorin ring, which comprises metering acrylonitrile at elevated temperature into a compound of the formula (II)

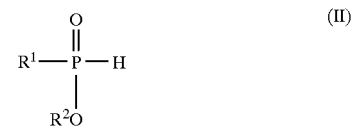

where $R^1$ and $R^2$ are as defined above.

8 Claims, No Drawings

PROCESS FOR THE PREPARATION OF 2-CYANOETHYLPHOSPHINIC ESTERS

The invention relates to a process for the preparation of 2-cyanoethylphosphinic esters.

2-Cyanoethylphosphinic esters are valuable intermediates in the preparation of $GABA_B$ antagonists (see European Patent 319 479, European Patent 319 482, Examples 5, 6, 7, 8, EP-A 463 560, Example 3). They are prepared by the addition reaction of acrylonitrile with phosphonous monoesters. The addition reaction is aided by alkali metal alcoholates. The two components are mixed at room temperature and the catalyst solution is added to this mixture. The reaction is then exothermic (Example 5: temperature rises to 100° C.). For safety reasons this method of preparation cannot be used for industrial purposes.

There was therefore a need to develop a process which avoids the aforementioned disadvantages, is industrially feasible without great expenditure and, moreover, makes the desired products available both in high yield and in high purity.

This object is achieved by a process for the preparation of phosphorus-containing compounds of the formula (I)

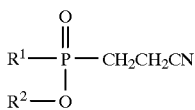

where $R^1$ and $R^2$ are identical or different and are a straight-chain or branched alkyl radical having 1 to 8 carbon atoms, a cyclohexyl-, cyclopentyl-, aryl-, halogen-, $(C_1-C_6)$-alkyl- or $(C_1-C_6)$-alkoxy-substituted aryl radical, where $R^1$ and $R^2$, together with the phosphorus atom and the oxygen atom, can also form a ring, in particular an oxaphosphorin ring, which comprises metering acrylonitrile at elevated temperature into a compound of the formula (II)

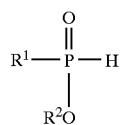

where $R^1$ and $R^2$ are as defined above.

The addition reaction of the acrylonitrile surprisingly proceeds without use of a catalyst. It is also surprising that at the high temperatures of the reaction the acrylonitrile undergoes polymerization or teleomerization only to a small extent or not at all, as is described for example in the presence of peroxides at 85° C. (U.S. Pat. No. 2,957,931, Example 55).

The process is important for example for reacting the following starting materials of the general formula (II): methanephosphonous monoethylester, methanephosphonous monobutylester, methanephosphonous monoamylester, phenylphosphonous monoethylester, phenylphosphonous monobutylester and 6H-dibenz[c,e][1,2]-oxaphosphorin-6-one. Such phosphonous monoesters can be prepared for example by the process in DE 19 604 195.

The process is advantageously carried out by metering acrylonitrile into the starting material of the formula (II) under an inert-gas atmosphere at 130–250° C., in particular 140–180° C., particularly preferably 155–170° C. The metering-in is carried out over a period of from 4 to 20 hours. The molar ratio of acrylonitrile to starting material of the formula (II) is advantageously from 0.4:1 to 1:1, preferably from 0.5:1 to 0.8:1. Any excesses of the starting materials of the formula (II) which may be present can frequently be removed by distillation. The crude products which remain are sufficiently pure for some reactions. If necessary, they can be purified by the known methods of distillation or crystallization.

EXAMPLE 1

120 g (2.26 mol) of acrylonitrile are added dropwise over 12 hours at 160° C. to 324 g (3.0 mol) of methanephosphonous monoethylester with vigorous stirring and under an inert-gas atmosphere. The excess monoester is then distilled off at 0.4 mbar. The residue is distilled using a Vigreux column at 142–143° C. at 0.4 mbar, giving 330 g of ethyl 2-cyanoethylmethylphosphinate (refractive index $n_D^{22}$: 1.4554). This corresponds to a yield of 90% of theory.

EXAMPLE 2

108 g (0.5 mol) of 6H-dibenz-[c,e][1,2]-oxaphosphorin-6-one are heated to 165° C. with stirring and under an inert-gas atmosphere, and 26.5 g (0.5 mol) of acrylonitrile are added dropwise over 4 hours. The mixture is stirred further at this temperature for 1 hour and then cooled, giving 134 g of a resinous composition. Digestion with a little acetonitrile produces 130 g of 6-(2-cyanoethyl)-(6H)-dibenz[c,e][1,2]-oxaphosphorin 6-oxide, which, after recrystallization from a little acetonitrile, has a melting point of 120–123° C. The yield is 97% of theory.

$C_{15}H_{12}NO_2P$ (269) Calc.: 66.92% C 4.46% H 5.20% N 11.5% P Found: 66.8% C 4.0% H 5.2% N 11.5% P

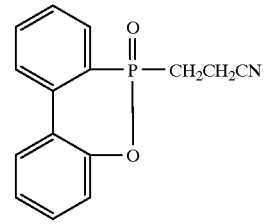

EXAMPLE 3

408 g (3.0 mol) of methanephosphonous mono-n-butylester are heated to 165° C. with vigorous stirring and under an inert-gas atmosphere, and 106 g (2.0 mol) of acrylonitrile are added dropwise over the course of 12 hours; the mixture is stirred further for 1 hour. It is then cooled and partially distilled at 0.3 mbar to an internal temperature of 130° C. The residue is distilled at a bath temperature of 155° C. and 0.2 mbar over a thin-film evaporator, giving 302 g of n-butyl 2-cyanoethylethylphosphinate having a purity of 96%. This corresponds to a yield of 80% of theory.

I claim:

1. A process for the preparation of phosphorus-containing compounds of the formula (I)

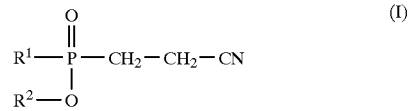

where $R^1$ and $R^2$ are identical or different and are a straight-chain or branched alkyl radical having 1 to 8 carbon atoms, a cyclohexyl-, cyclopentyl-, aryl-, halogen-, ($C_1$–$C_6$)-alkyl- or ($C_1$–$C_6$)-alkoxy-substituted aryl radical or, where $R^1$ and $R^2$, together with the phosphorus atom and the oxygen atom, form a ring, which comprises metering acrylonitrile at a temperature from 130–250° C. into a compound of the formula (II)

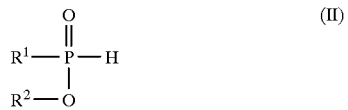

where $R^1$ and $R^2$ are as defined above and said process proceeds without a catalyst.

2. The process as claimed in claim 1, wherein the starting material of the formula (II) is methanephosphonous monoethylester, methane-phosphonous monobutylester, methanephosphonous monoamylester, phenyl-phosphonous monoethylester, phenylphosphonous monobutylester or 6H-dibenz[c,e][1,2]-oxaphosphorin-6-one.

3. The process as claimed in 1, wherein the molar ratio of acrylonitrile to starting material of the formula (II) is from 0.4:1 to 1:1.

4. The process as claimed in 1, wherein the metering-in is carried out over a period of from 4 to 20 hours.

5. The process as claimed in claim 1, wherein $R^1$ and $R^2$ together form an oxaphosphorine ring.

6. The process according to claim 2, wherein the acrylonitrile is metered in at from 140 to 180° C.

7. The process as claimed in claim 1, wherein the acrylonitrile is metered in at from 155 to 170° C.

8. The process as claimed in claim 6, wherein the molar ratio of acrylonitrile to starting material of the formula (II) is from 0.5:1 to 0.8:1.

* * * * *